United States Patent
Koziak et al.

(10) Patent No.: US 6,884,429 B2
(45) Date of Patent: Apr. 26, 2005

(54) MEDICAL DEVICES INCORPORATING DEUTERATED RAPAMYCIN FOR CONTROLLED DELIVERY THEREOF

(75) Inventors: Joseph Koziak, Scottsdale, AR (US); Selvaraj Naicker, Edmonton (CA); Randall W. Yatscoff, Edmonton (CA); Robert T. Foster, Edmonton (CA)

(73) Assignee: Isotechnika International Inc., Bridgetown (BB)

( * ) Notice: Subject to any disclaimer, the term of this patent is extended or adjusted under 35 U.S.C. 154(b) by 360 days.

(21) Appl. No.: 10/301,504

(22) Filed: Nov. 20, 2002

(65) Prior Publication Data

US 2003/0130206 A1 Jul. 10, 2003

Related U.S. Application Data

(63) Continuation-in-part of application No. 09/987,812, filed on Nov. 16, 2001, now Pat. No. 6,503,921, which is a continuation of application No. 09/348,015, filed on Jul. 6, 1999, now Pat. No. 6,342,507, which is a continuation-in-part of application No. 09/148,623, filed on Sep. 4, 1998, now abandoned.

(60) Provisional application No. 60/057,632, filed on Sep. 5, 1997.

(51) Int. Cl.[7] ............................ A61M 25/00; A61F 2/00
(52) U.S. Cl. ........................................ 424/423; 604/265
(58) Field of Search ...................... 514/1; 424/1; 604/1

(56) References Cited

U.S. PATENT DOCUMENTS

| | | | |
|---|---|---|---|
| 5,288,711 A | * | 2/1994 | Mitchell et al. ............... 514/56 |
| 5,665,728 A | | 9/1997 | Morris et al. |
| 6,153,252 A | | 11/2000 | Hossainy et al. |
| 6,273,913 B1 | | 8/2001 | Wright et al. |
| 6,335,029 B1 | | 1/2002 | Kamath et al. |
| 6,342,507 B1 | * | 1/2002 | Naicker et al. ............. 514/291 |
| 6,503,921 B2 | * | 1/2003 | Naicker et al. ............. 514/291 |
| 6,710,053 B2 | * | 3/2004 | Naicker et al. ............. 514/291 |
| 2001/0027340 A1 | | 10/2001 | Wright et al. |
| 2002/0123505 A1 | | 9/2002 | Mollison et al. |

FOREIGN PATENT DOCUMENTS

WO    WO 95/26325    10/1995

* cited by examiner

*Primary Examiner*—Thurman K. Page
*Assistant Examiner*—Casey Rosenthal
(74) *Attorney, Agent, or Firm*—Fish & Richardson P.C.

(57) ABSTRACT

Deuterated rapamycin can be controllably introduced target locations within the patient's body by using an implantable medical device having a structure incorporated with a therapeutic agent comprising a deuterated rapamycin. Representative deuterated rapamycins include epi-7-deuteromthyl rapamycin, 7,43-$d_6$ rapamycin, 7-deuteromethyl rapamycin and 31,42-$d_2$-rapamycin and isomers thereof, and mixtures thereof. The deuterated rapamycin can also be glycosylated.

11 Claims, 3 Drawing Sheets

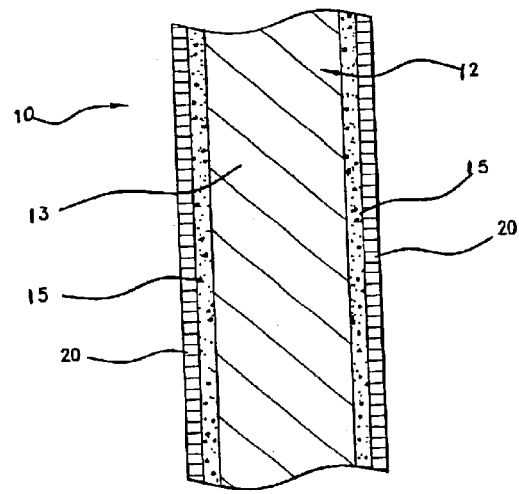
FIG.1
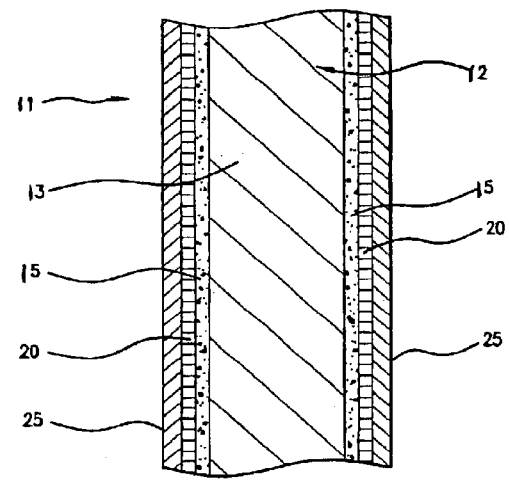
FIG. 2
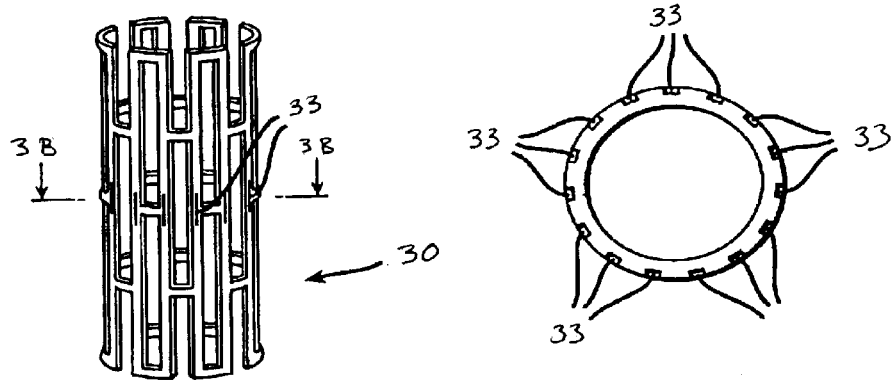
FIG 3A
FIG 3B

MEDICAL DEVICES INCORPORATING DEUTERATED RAPAMYCIN FOR CONTROLLED DELIVERY THEREOF

REFERENCE TO RELATED APPLICATIONS

This application is a continuation-in-part of U.S. patent application Ser. No. 09/987,812 filed Nov. 16, 2001, now U.S. Pat. No. 6,503,921,which is a continuation of U.S. patent application Ser. No. 09/348,015 filed Jul. 6, 1999, now U.S. Pat. No. 6,342,507 which is continuation-in-part of U.S. patent application Ser. No. 09/148,623 filed on Sep. 4, 1998 now abandoned, which is based on provisional patent application No. 60/057,632 filed on Sep. 5, 1997, all of which are relied on and incorporated herein by reference.

FIELD OF THE INVENTION

The present invention relates to methods and medical devices for the controlled, localized delivery of deuterated rapamycin within a body.

BACKGROUND OF THE INVENTION

This invention relates to deuterated derivatives of rapamycin and methods for delivering and using them in the treatment of transplantation rejection, host vs. graft disease, graft vs. host disease, leukemia/lymphoma, hyperproliferative vascular disorders, autoimmune diseases, diseases of inflammation, solid tumors, and fungal infections.

Rapamycin, known as sirolimusis, is a 31-membered macrolide lactone, $C_{51}H_{79}NO_{13}$, with a molecular mass of 913.6 Da. In solution, sirolimus forms two conformational trans-, cis-isomers with a ratio of 4:1 (chloroform) due to hindered rotation around the pipecolic acid amide bond. It is sparingly soluble in water, aliphatic hydrocarbons and diethyl ether, whereas it is soluble in alcohols, halogenated hydrocarbons and dimethyl sulfoxide. Rapamycin is unstable in solution and degrades in plasma and low-, and neutral -pH buffers at 37° C. with half-life of <10 h. the structures of the degradation products have recently been characterized. Rapamycin is a macrocyclic triene antibiotic produced by *Streptomyces hygroscopicus*, which was found to have antifungal activity, particularly against *Candida albicans*, both in vitro and in vivo, C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. Nos. 3,929,992; and 3,993,749.

Rapamycin alone (U.S. Pat. No. 4,885,171) or in combination with picibanil (U.S. Pat. No. 4,401,653) has been shown to have antitumor activity. R. Martel et al., Can. J. Physiol. Pharmacol. 55, 48 (1977), disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection, FASEB 3, 3411 (1989); FASEB 3, 5256 (1989); and R. Y. Calne et al., Lancet 1183 (1978). Although it shares structural homology with the immunosuppressant tacrolimus and binds to the same intracellular binding protein in lymphocytes, rapamycin inhibits S6p70-kinase and therefore has a mechanism of immunosuppressive action distinct from that of tacrolimus. Rapamycin was found to prolong graft survival of different transplants in several species alone or in combination with other immunosupressants. In animal models its spectrum of toxic effects is different from that of cyclosporin or FK-506, comprising impairment of glucose homeostasis, stomach, ulceration, weight loss and thrombocytopenia, although no nephrotoxicity has been detected.

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. Carboxylic acid esters (PCT application No. WO 92/05179), carbamates (U.S. Pat. No. 5,118,678), amide esters (U.S. Pat. No. 5,118,678), (U.S. Pat. No. 5,118,678) fluorinated esters (U.S. Pat. No. 5,100, 883), acetals (U.S. Pat. No. 5,151,413), silyl ethers (U.S. Pat. No. 5,120,842), bicyclic derivatives (U.S. Pat. No. 5,120,725), rapamycin dimers (U.S. Pat. No. 5,120,727) and O-aryl, O-alkyl, O-alkyenyl and O-alkynyl derivatives (U.S. Pat. No. 5,258,389) have been described.

Rapamycin is metabolized by cytochrome P-450 3A to at least six metabolites. During incubation with human liver and small intestinal microsomes, sirolimus was hydroxylated and demethylated and the structure of 39-O-demethyl sirolimus was identified. In bile of sirolimus-treated rats >16 hydroxylated and demethylated metabolites were detected.

In rapamycin, demethylation of methoxy group at C-7 Carbon will lead to the change in the conformation of the rapamycin due to the interaction of the released C-7 hydroxyl group with the neighbouring pyran ring system which is in equilibrium with the open form of the ring system. The C-7 hydroxyl group will also interact with the triene system and possibly alter the immunosupressive activity of rapamycin. This accounts for the degradation of rapamycin molecule and its altered activity.

Stable isotopes, e.g., deuterium, $^{13}C$, $^{15}N$, $^{18}O$, are non-radioactive isotopes which contain one additional neutron than the normally abundant isotope of the atom in question. Deuterated compounds have been used in pharmaceutical research to investigate the in vivo metabolic fate of the compounds by evaluation of the mechanism of action and metabolic pathway of the non deuterated parent compound. (Blake et al. J. Pharm. Sci. 64, 3, 367–391,1975). Such metabolic studies are important in the design of safe, effective therapeutic drugs, either because the in vivo active compound administered to the patient or because the metabolites produced from the parent compound prove to be toxic or carcinogenic (Foster et al., Advances in drug Research Vol. 14, pp. 2–36, Academic press, London, 1985).

Incorporation of a heavy atom particularly substitution of deuterium for hydrogen, can give rise to an isotope effect that can alter the pharmacokinetics of the drug. This effect is usually insignificant if the label is placed in a molecule at the metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another tom will best stronger than the same bond between the light isotope and that atom. In any reaction in which the breaking of this bond is the rate limiting step, the reaction will proceed slower for the molecule with the heavy isotope due to kinetic isotope effect. A reaction involving breaking a C—D bond can be up to 700 percent slower than a similar reaction involving breaking a C—H bond.

More caution has to be observed when using deuterium labeled drugs. If the C—D bond is not involved in any of the steps leading to the metabolite, there may not be any effect to alter the behavior of the drug. If a deuterium is placed at a site involved in the metabolism of a drug, an isotope effect will be observed only if breaking of the C—D bond is the rate limiting step. There are evidences to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway by a process called "metabolic switching".

It is also observed that one of the most important metabolic pathways of compounds containing aromatic systems is hydroxylation leading to a phenolic group in the 3 or 4 position to carbon substituents. Although this pathway involves cleavage of the C—H bond, it is often not accompanied by an isotope effect, because the cleavage of this bond is mostly not involved in the rate-limiting step. The substitution of hydrogen by deuterium at the stereo center will induce a greater effect on the activity of the drug.

Clinically relevant questions include the toxicity of the drug and its metabolite derivatives, the changes in distribution or elimination (enzyme induction), lipophilicity which will have an effect on absorption of the drug. Replacement of hydrogen by deuterium at the site involving the metabolic reaction will lead to increased toxicity of the drug. Replacement of hydrogen by deuterium at the aliphatic carbons will have an isotopic effect to a larger extent. Deuterium placed at an aromatic carbon atom, which will be the site of hydroxylation, may lead to an observable isotope effect, although this is less often the case than with aliphatic carbons. But in few cases such as in penicillin, the substitution on the aromatic ring will induce the restriction of rotation of the ring around the C—C bond leading to a favorable stereo-specific situation to enhance the activity of the drug.

Approaching half a century of stable-isotope usage in human metabolic studies has been without documented significant adverse effect. Side-effects with acute D dosing are transitory with no demonstrated evidence of permanent deleterious action. The threshold of D toxicity has been defined in animals and is far in excess of concentrations conceivably used in human studies (Jones P J, Leatherdale S T Clin Sci (Colch) April 1991; 80(4):277–280). The possibility that D may have additional beneficial pharmacological applications cannot be excluded. For isotopes other than D, evidence of observed toxicity remains to be produced even at dosages far in excess of the range used in metabolic studies. Absence of adverse effect may be attributable to small mass differences and the similar properties of tracer and predominantly abundant isotopes. The precision of extrapolating toxicity thresholds from animal studies remains unknown. However, should perturbation of the delicate homoeostatic characteristic of living organisms occur with use of stable isotopes, it is almost undoubtedly at some level of administration greatly in excess of those administered currently in biomedical research.

The prior art does not disclose specifics regarding deuterating rapamycin for improving the stability of the rapamycin molecule. The art also fails to teach that glycosylating deuterated rapamycin enhances the rapamycin's stability and solubility which ultimately increases the molecule's bio-availability. Therefore, the invention is directed to rapamycin derivatives which are more stable, less prone to degradation, and more water soluble than rapamcin and to techniques for delivering such agents.

SUMMARY OF THE INVENTION

The present invention is based in part on the recognition that deuterated rapamycin's effectiveness can be significantly enhanced by incorporating deuterated rapamycin onto the surface or structures of implantable medical devices that are partly or completely introduced into a body cavity such as the vascular system, esophagus, trachea, colon, biliary tract, urinary tract, or other location within a human or veterinary patient. For example, many treatments of the vascular system entail the introduction of a device such as a stent, catheter, balloon, guide wire, cannula or the like. With the present invention precise amounts of deuterated rapamycin can be introduced locally during or following a medical procedure.

In one aspect, the invention is directed to an implantable medical device having a structure adapted for introduction into a patient, wherein the structure incorporates with a therapeutic agent comprising a deuterated rapamycin.

Preferred deuterated rapamycins are selected from the group consisting of epi-7-deuteromthyl rapamycin, 7,43-$d_6$ rapamycin, 7-deuteromethyl rapamycin and 31,42-$d_2$-rapamycin and isomers thereof, and mixtures thereof. Tthe deuterated rapamycin can be glycosylated.

BRIEF DESCRIPTION OF THE DRAWINGS

FIGS. 1 and 2 are cross sectional views of coated medical devices;

FIGS. 3A and 3B are elevational and cross sectional view, respectively, of a stent having channels on its surface of storing deuterated rapamycin;

DETAILED DESCRIPTION OF PREFERRED EMBODIMENTS

Figure 4:
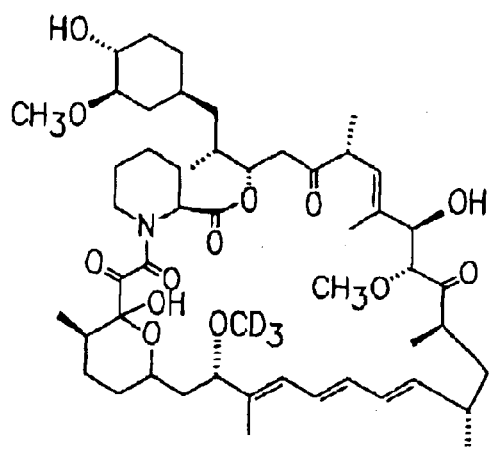
FIG. 4 is the chemical structure of 7-deuteromethyl rapamycin showing sites of deuteration.
Figure 5:
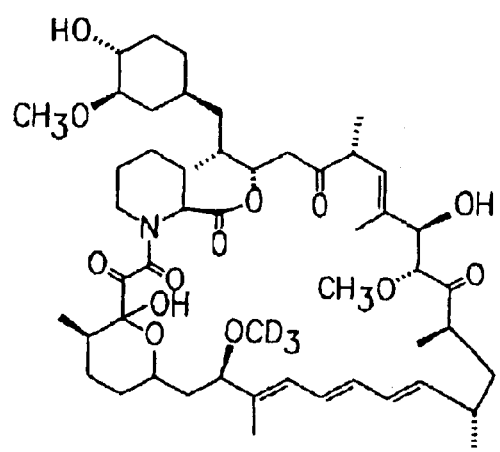
FIG. 5 is the chemical structure of epi-7 deuteromethyl rapamycin showing sites of deuteration.
Figure 6:
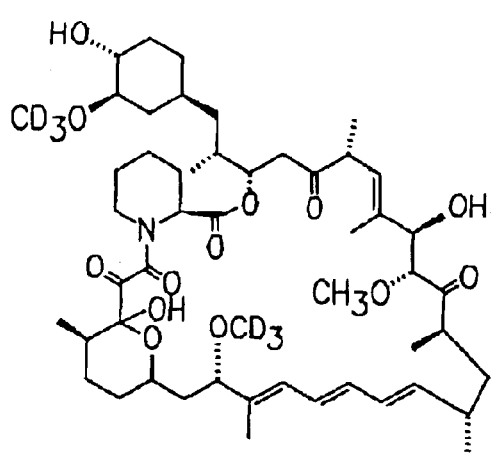
FIG. 6 is the chemical structure of 7,43-$d_6$-rapamycin showing sites of deuteration.

The present invention provides implantable medical devices and methods for the controlled, localized delivery of deuterated rapamycin to target locations within the body of a patient. The term "controlled localized delivery" as used herein is defined as a characteristic release rate of the deuterated rapamycin over a desired period of time at a fixed location. The implantable medical devices of the present invention may have a simple construction, provide a minimal cross-sectional profile, and allow for easy and reproducible loading of the deuterated rapamycin. The terms "bioactive agent" and "bioactive material" are used interchangeably.

Various techniques can be employed to deliver deuterated rapamycin from the medical devices. For example, deuterated rapamycin-polymers mixtures can be coated to the surface of medical devices to hold the drug for release.

Another method is to entrap the drug into the structure of the medical device which has been modified to contain micropores, channels, or reservoirs. Finally, deuterated rapamycin can be covalently bound to the medical device surface via solution chemistry techniques or dry chemistry techniques and combinations thereof. While the invention will be illustrated using modified stents and grafts, it is understood that the inventive techniques are applicable to medical devices in general as further discussed herein.

Medical Device Coated with Deuterated Rapamycin

With reference to FIG. 1, an implantable medical device 10 in accordance with the present invention is shown and includes a structure 12 adapted for introduction into a patient. The term "adapted" is used herein to mean that the structure 12 is shaped and sized for such introduction. For clarity, only a portion of structure 12 is shown.

By way of example, structure 12 is configured as a stent particularly adapted for insertion into the vascular system of the patient. As known in the art, stents are tubular support structures that are implanted in coronary and peripheral blood vessels or arteries or other non-vascular lumens, blood vessels or other tubular body lumens. The present invention can thus be used for the dual purpose of localized drug delivery and stent placement, for example. The stent structure may also be used in non-vascular systems and sites such as the esophagus, trachea, colon, biliary ducts, urethra, and ureters, among others.

Referring to FIG. 1, structure 12 can alternatively be configured as any conventional vascular or other medical device, and includes any of a variety of conventional stent or other adjuncts, such as helically wound strands, perforated cylinders or the like. Accordingly, the structure 12 is configured as at least one, or any portion of, a medical device that is adapted for insertion into the body. Examples of such medical devices include catheters, guide wires, balloons, filters (e.g., vena cava filters), stents, stent grafts, vascular grafts, intraluminal paving systems, implants and other devices used in connection with drug-loaded polymer coatings. Such devices are implanted or otherwise utilized in body lumens and organs such as the coronary vasculature, esophagus, trachea, colon, biliary tract, urinary tract, prostate, brain, and the like. Examples of suitable vascular grafts are described in U.S. Pat. Nos. 5,509,931, 5,527,353, and 5,556,426. Vena cava filters such as those described in WO 96/12448 and WO 96/17634 may also be used in the present invention. All of foregoing patents are incorporated herein by reference.

The grafts, including stent grafts, that are provided with a deuterated rapamycin-polymer composite layer in accordance with the present invention include synthetic vascular grafts that are used for replacement of blood vessels in part or in whole. A typical vascular graft is a synthetic tube with each end thereof sutured to the remaining ends of a blood vessel from which a diseased or otherwise damaged portion has been removed. In a typical stent graft, each end of the synthetic tube portion includes a stent that is affixed to each of the remaining ends of a blood vessel from which a diseased or otherwise damaged portion has been removed. Alternatively in a stent graft, the replacement vessel may be a segment of a vessel removed from another location in the patient, such as a portion of a femoral artery or the like. In the case of a synthetic graft, the graft is typically tubular and may be, e.g., of a woven, knit or velour construction. Preferred base materials for the grafts and covering material for the stent grafts include polyethylene terephthalate and polytetrafluoroethylene. The vascular grafts may be reinforced with, for example, helices, rings, etc. in order to provide uniform strength over the entire surface of the graft tubing. The materials with which such grafts are constructed are biologically compatible materials including, but not limited to, thermoplastic materials such as polyester, polytetrafluoroethylene (PTFE), silicone and polyurethanes. The preferred materials include polyester fibers and PTFE.

Examples of other suitable grafts are described in U.S. Pat. Nos. 5,509,931, 5,527,353, and 5,556,426, all of which are incorporated herein by reference. In a preferred embodiment of the invention, the graft is provided with a composite layer of polymeric material/deuterated rapamycin. This polymer/deuterated rapamycin composite-coated graft, when positioned at a desired site in the body provides an extended release of deuterated rapamycin to the site.

Referring to FIG. 1, structure 12 includes a base material 13 which is compatible with the intended use of structure 12. The base material 13 is preferably biocompatible. A variety of conventional materials may be employed as the base material 13. For example, the base material 13 may be either elastic or inelastic. The base material 13 may be either biodegradable or nonbiodegradable.

Accordingly, the base material 13 may be formed of stainless steel, tantalum, titanium, NITINOL®, gold, platinum, inconel, iridium, silver, tungsten, or another biocompatible metal, or alloys of any of these; carbon or carbon fiber; cellulose acetate, cellulose nitrate; silicone, polyethylene terephthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these. Stainless steel and NITINOL® are particularly useful as base materials when the structure 12 is configured as a vascular stent.

The implantable medical device 10 may also include at least one layer 15 formed by a composite of deuterated rapamycin and a biocompatible polymeric or copolymeric material. When multiple polymer-deuterated rapamycin composite layers are used, the layers may contain the same or different deuterated rapamycins and/or the same or different polymers. The combination of deuterated rapamycin and polymer serves as a monolithic matrix depot of the deuterated rapamycin. This depot contributes partially to providing control over the release rate of the deuterated rapamycin from the medical device.

The composite layer(s) are formed from a solution or dispersion (e.g. suspension, emulsion, or semisolid) which is applied to at least a portion of the surface of the base material 13 to form the polymer-deuterated rapamycin composite layer 15. The application of polymer-deuterated rapamycin composite 15 onto at least a portion of the base materials 13 may be accomplished by a physical method such as, but not limited to, spraying, dipping, painting, electrostatic interaction, physical adsorption or covalent method such as, but not limited to, chemical attachment to the base material 13. The polymer-deuterated rapamycin composite layer 15 is preferably capable of incorporating a substantial amount of deuterated rapamycin, such as, for example, 0.2 $\mu g/mm^2$ to 20 $\mu g/mm^2$. The percent of drug in composite layer 15 can be varied from 1% to 50% w/w. The polymer-deuterated rapamycin composite layer 15 is typically applied at a thickness of greater than 1 micron, preferably a thickness of about 5–50 microns and most preferably a thickness of about 5 to 25 microns in order to adjust the deuterated rapamycin dosage. Very thin polymer-deuterated rapamycin composites, e.g., of about 0.2–0.3 microns are also possible, optionally, multiple layers of polymer-deuterated rapamycin composites may be applied onto the outer surface of the base material (or part(s) thereof) 13 of structure 12. Such multiple layers can be of the same or different polymer materials and/or deuterated rapamycins.

The biocompatible polymeric material used to form the deuterated rapamycin-polymer composite layer(s) may include any polymeric material capable of forming a solidified composite layer in the presence of the deuterated rapamycin. The polymeric material of the present invention is hydrophilic or hydrophobic, and is, for example, polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, polyolefins, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions, (e.g., BAYHDROL®, and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. Composite layer 15 can include of a single polymer or copolymer. It may also include copolymers or physical blends of any of the materials indicated above. In one embodiment of the invention, the polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids.

The use of the deuterated rapamycin-polymer composite layer 15 in the present invention has the added advantage in that this layer or multilayers allow for enhanced adhesion of the mixture to the base material 13. The deuterated rapamycin-polymer composite layer 15 also provides for an effective way of adjusting the amount of the deuterated rapamycin placed on the base material 13. This is accomplished by adjusting the deuterated rapamycin/polymer ratio and/or thickness of the deuterated rapamycin-polymer composite layer. Also, composite layer 15 provides a co-compliant surface for a subsequent barrier layer and aids in maintaining the mechanical integrity of the barrier layer during the expansion of the medical device. The deuterated rapamycin-polymer composite also has the added benefit of providing a blood compatible surface to the medical device. Thus, the biocompatible polymer material acts as an intermediary between the vascular walls or the blood stream and the implantable medical device 10.

The release profile of the drug from the deuterated rapamycin-polymer composite layer 15 is determined by many factors including the drug solubility, the amount of the drug applied, the drug-to-polymer ratio in composite layer 15 and the thickness and porosity of the composite layer. The release profile is also regulated by the presence of an outer barrier layer which is formed by a vapor deposition process or a low energy plasma polymerization process.

Still with reference to FIG. 1, implantable medical device 10 of the present invention may also include at least one barrier layer 20 positioned over the deuterated rapamycin-polymer composite layer(s) 15. One purpose of this barrier layer or layers is to provide further controlled release of the deuterated rapamycin when device 10 is positioned in the vascular system or other body lumen of a patient. The thickness of the barrier layer 20 is chosen so as to provide such control. Also, the barrier layer 20 protects the drug from the routine handling process and physiologic environment until the drug reaches the target site.

The barrier layer 20 is a polymer or copolymer layer deposited on the outer surface of the deuterated rapamycin-polymer composite layer 15 by a vapor deposition process or a low energy plasma polymerization process. Low-energy plasma polymerization is performed by exposing the composite coated implantable medical device to a monomer gas at the inception of the plasma polymerization process. The deuterated rapamycin-polymer composite-coated device is placed in a plasma chamber or other similar device and exposed to a monomer gas such as, for example, silicone-based monomers such as cyclic or acyclic siloxanes, silanes, silylimidazoles; fluorine-based monomers such as hydrofluorocarbons; aliphatic or aromatic hydrocarbons; acrylic monomers; N-vinyl pyrrolidone; ethylene oxide or combinations thereof. The monomer gas may have functional groups to allow covalent attachment of appropriate drugs by anchoring to these functional groups. Polymer blends, copolymers, or interpenetrating networks can be deposited in addition to homopolymer deposition, by simultaneous or subsequent introduction of two or more monomer gases. When introduced as a mixture, the ratio of the monomer gases could be adjusted to obtain desired properties. An energy source such as a radio frequency energy source is used to produce the low energy generating process.

Alternatively, the barrier layer can be applied by the vapor deposition process. Examples of polymers that can be deposited in such a manner are parylene or polyamides. For deposition of parylene using this process, the monomer vapor of p-xylylene formed by high temperature pyrolysis of its dimer form, is condensed at temperatures of 50° C. or lower on the surface of composite layer 15 to form the barrier layer polymer.

Low-energy plasma generates active species in a circulating monomer gas, a polymer is formed and is subsequently deposited on the outer surface of the previously-coated device. The plasma may also generate active species on the device to be coated along with the monomer gas. This leads to plasma grafting in addition to plasma polymerization. Properties of the low-energy plasma polymerization barrier layer, i.e., the thickness and/or cross-linking density of the formed polymer, are controlled, for example, by the monomer flow rate, pressure and power of the plasma supplied, reaction time, and combinations thereof in a manner such that the properties of the deuterated rapamycin are not negatively effected.

The use of low-energy plasma polymerization provides for elimination of thermal effects of typical polymerization methods because the low-energy process occurs at room temperature. Also, since the monomer is introduced in a gaseous form, in the plasma chamber, no solvents are necessary for the application to the deuterated rapamycin-composite layer. Furthermore, since the time frame used for the low-energy process is small, the possibility of any adverse effects to the deuterated rapamycin is minimal.

Another function of barrier layer 20 is to provide protection of the deuterated rapamycin-polymer composite layer 15 from damage that may occur, e.g., from handling of the device, such as during maneuvering of the device through the body until it is placed at the desired target site. This could be achieved in one or more different way.

For example, the plasma polymerization process allows covalent anchoring of the barrier layer 20 to the polymer matrix in the composite layer 15. The formation of covalent bonds between the composite layer 15 and the barrier layer 20 subsequently offers a stronger adhesion of the barrier layer 20 and hence an enhanced protection of the drug depot in the composite layer 15.

Also, in the case of a hydrophobic barrier layer, the diffusion of water from the physiologic environment is restricted, thus limiting contact of the deuterated rapamycin with the eluting environment.

Additionally, the barrier layer formed by plasma polymerization is cross-linked in nature and the degree of cross-linking can be varied by varying the plasma polymerization process parameters, such as the power. An added endurance could be obtained by increasing the cross-linking density and hence a more rigid barrier layer, while lowering the cross-linking density provides a more flexible barrier layer.

The at least one barrier layer 20 of the present invention is preferably less than 5000 Å thick and preferably about 50–2000 Å thick.

In an alternative embodiment, a deuterated rapamycin or other bioactive material is incorporated into or on the outer surface of the barrier layer. For example, a second bioactive material is introduced into the barrier layer 20 by any suitable method. FIG. 2 shows a stent having an outer coating of bioactive agent, such as heparin, which is applied to barrier layer 20 to produce layer 25. The outer bioactive agent, which in this case is different from the deuterated rapamycin of the deuterated rapamycin-polymer composite layer, is placed in solution and applied to the barrier layer 20 by any suitable means, including dipping the coated medical device into the drug solution or by applying the solution onto the layer 20 such as by spraying. In the former method, the amount of bioactive agent loading is controlled by regulating the time the barrier layer is exposed to the drug solution or dispersion, the extent of polymer cross-linking, the concentration of the drug in the solution or dispersion and/or the amount of barrier layer applied to the medical device.

The barrier layer with the second bioactive agent may have a similar composition or may differ physically or chemically from the first barrier layer. The nature of the second barrier layer would be dictated by the physicochemical properties of the bioactive agent to be incorporated on the outer surface.

In the event that the deuterated rapamycin used in the layer 15 is the same as the bioactive agent in layer 20, the deuterated rapamycin of layer 15 provides an initial bolus loading dose required to reach the therapeutic window, which is further maintained by the deuterated rapamycin-polymer composite layer 15.

In the event that the deuterated rapamycin of layer 15 is different from the bioactive agent used with layer 20, the bioactive agent in layer 20 provides a combination of biological effects achieved by either a synergistic or independent bioactivity of the two bioactive materials.

When implanted, a substantial amount of the deuterated rapamycin contained in the deuterated rapamycin-polymer composite layer 15 of the medical device is diffused into the affected area over an extended period of time and in a controlled manner.

Medical Device Having Channels Containing Deuterated Rapamycin

The surface of medical devices can be fabricated with structures for storing deuterated rapamycin for subsequent release. These storage structures referred to generally as channels or reservoirs can having any suitable configuration.

As an illustration, FIGS. 3A and 3B stent strut 30 are modified to have a plurality elongated channels 33. A technique for incorporating deuterated rapamycin inside the channel is to immerse the modified stent into a deuterated rapamycin solution, e.g., acetone or methylene chloride as the solvent, for sufficient time to allow solution to permeate into the channels. After solvent has been allowed to evaporate, the stent is dipped briefly in fresh solvent to remove excess surface bound drug. A solution of polymer is applied to the stent to form an outer layer of polymer which acts as a diffusion-controller for release of the deuterated rapamycin.

Medical Device Having Deuterated Rapamycin Covalently Bonded to Surface

The surface of medical devices can chemically derivatized to allow covalent immobilization of deuterated rapamycin that is later released upon lysis of the covalent drug tether. For example, deuteratred rapamycin can modified to contain a hydrolytically or enzymatically labile covalent bond for attaching to the surface of the stent. Covalent bonds such as ester, amides or anhydrides may be suitable for this.

Synthesis of Deuterated Rapamycin

FIGS. 4–7 show examples of sites for deuteration of the rapamycin molecule. Nonlimiting examples of deuterated rapamycin molecules include the compounds; 7-deuteromethyl rapamycin (FIG. 4), epi-7-deuteromethyl rapamycin (FIG. 5), 7,43-$d_6$-rapamycin (FIG. 6) and 31,42-$d_2$-rapamycin (FIG. 7) including the cis and trans isomers of the compounds shown in FIGS. 4–7. FIG. 8 shows the preparation and structure of the compound glycosylated deuterorapamycin.

EXAMPLE 1

Preparation of 7-Deuteromethyl Rapamycin (FIG. 4)

5 mg of Rapamycin was dissolved in 2.5 ml of dichloromethane. 40 mg of deuterated methanol was added. 10 beads of NAFION® catalyst were added to the above solution. The contents were stirred under nitrogen at room temperature for 14 hours. The reaction was monitored by mass spectrum. The solution was filtered and concentrated The residue was dissolved in dry benzene and freeze dried. The white solid obtained was homogenous by mass spectrum analysis and characterized by LC/MS.

EXAMPLE 2

Figure 7:
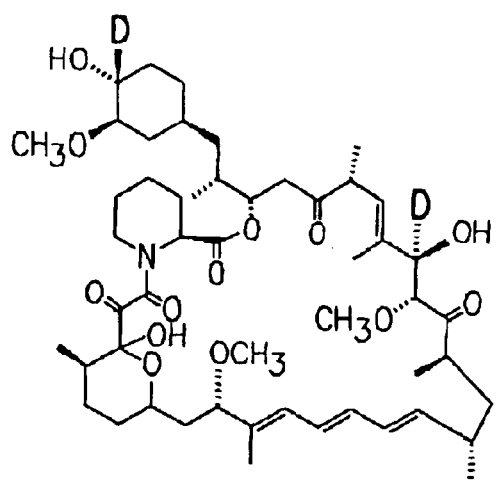
FIG. 7 is the chemical structure of 31,42-$d_2$ showing sites of deuteration.
Figure 8:
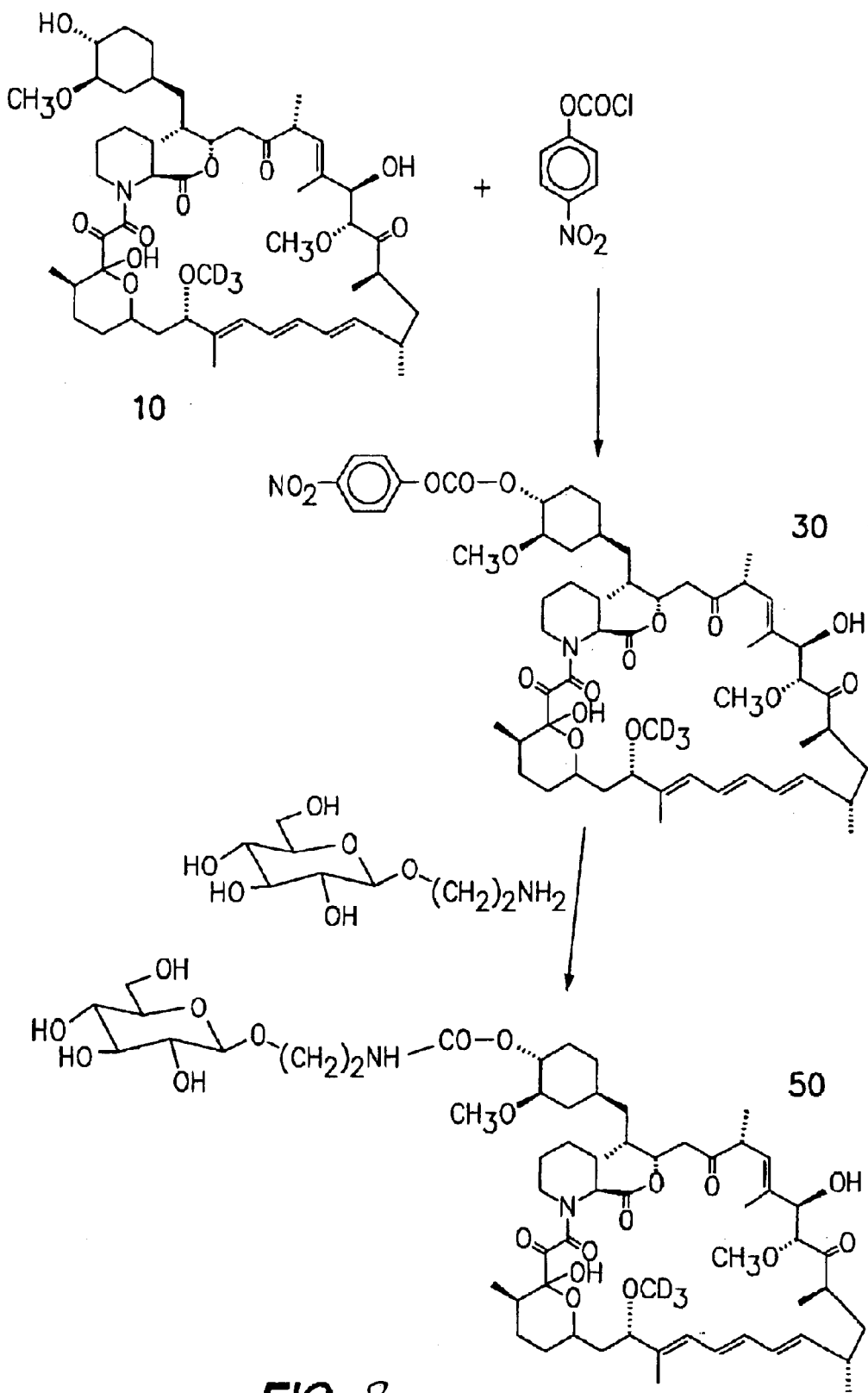
FIG. 8 illustrates the preparation of glycosylated deuterorapamycin.

Preparation of 31, 42 $d_2$-7-deuterated Rapamycin (FIG. 7)

Rapamycin (11 mM) was dissolved in a mixture of cyclohexane and dichloromethane (1:1) 10 ml. The contents were cooled in ice bath and poly(vinylpyridinium) dichromate 0.5 grams was added. The reaction mixture was stirred overnight and the reaction was followed by mass spectrum. The reaction mixture was filtered, washed with water and dried using anhydrous magnesium sulphate. The organic solution was filtered and concentrated. The crude product was subjected to purification by silica column using chloroform-methanol (20:10) mixture.

The pure fractions were collected and concentrated. The residue was dissolved in benzene and freeze dried. The product was characterized by LC/MS. M+(Na) 932. This material was dissolved in dry ether (10 ml). 10 equivalents of lithium aluminum deuteride was added. The reaction mixture was stirred for 24 hours. After the completion of the reaction, the excess of LiAlD$_4$ was decomposed by the addition of acetone. The complex was decomposed by adding ice cooled acetic acid.

The mixture is filtered. The filtrate was diluted with ether and washed with water, dried, and concentrated. The crude mixture was subjected to column chromatography and the required material was eluted using chloroform-methanol solvent system. The pure fractions were collected and concentrated. The compound was tested by mass spectrum. M=(Na) 940. This compound was converted to the desired final compound (2) by following the procedure as described in Example 1.

EXAMPLE 3
Preparation of Glycosylated deuteroRapamycin (FIG. 8)

Referring to FIG. 8, compound 10 prepared by example 1 (20 mg) was dissolved in 5 ml of dichloromethane. Dimethylaminopyridine (2.2 mg) was added to the above solution. The contents were cooled to −70° C.

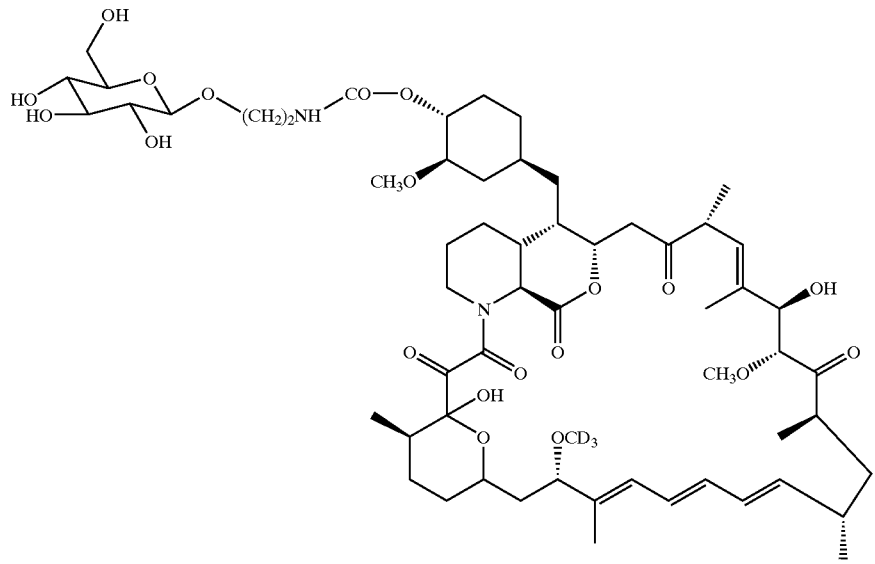

4-Nitrophenylchloroformate in dichloromethane was added to the reaction mixture. The solution was stirred under nitrogen at room temperature for 14 hours. The reaction was followed by mass spectrum. After the completion of the reaction, the reaction mixture was diluted with dichloromethane and the organic solution was washed with water, 0.2M ice cold HCl solution. The organic layer was dried over anhydrous magnesium sulphate. After filtration, the organic solution was filtered and concentrated. The crude product was purified by LC/MS to provide the pure compound 30 (Yield 10 mg.) Compound 30 (0.9 m.mol)was dissolved in dry DMF(0.5 ml) To this mixture, a solution of 2-aminoethyl-a-D-glucopyranoside (7.2 m.mol) was added. The reaction mixture was stirred for 14 hours at room temperature. After the completion of the reaction, the mixture was diluted with dichloromethane. The organic solution was concentrated in vacuum. The residue was extracted with water and the aqueous solution was subjected to biogel column to get the required pure compound 50. This material was characterized by LC/MS. M+(Na)1185.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. An implantable medical device having a structure adapted for introduction into a patient, wherein the structure coated, entrapped, or covalently bonded is with a therapeutic agent comprising a deuterated rapamycin.

2. The medical device of claim 1 wherein the deuterated rapamycin is selected from the group consisting of epi-7-deuteromthyl rapamycin, 7,43-$d_6$ rapamycin, 7-deuteromethyl rapamycin, 31,42-$d_2$-rapamycin, isomers thereof, and mixtures thereof.

3. The medical device of claim 1 wherein the deuterated rapamycin is glycosylated.

4. The medical device of claim 3 wherein the deuterated rapamycin is glycosylated at position 42.

5. The medical device of claim 4 wherein the glycosylated deuterated rapamycin has the structure:

6. The medical device of claim 1 wherein the medical device is coated with the deuterated rapamycin.

7. The medical device of claim 1 wherein the structure includes a surface having one or more channels formed thereon wherein the one or more channels contain the deuterated rapamycin.

8. The medical device of claim 1 wherein:
    (i) the structure comprises a base material; and
    (ii) at least one layer comprised of deuterated rapamycin in a polymer matrix, applied to at least a portion of the outer surface of said base material.

9. The medical device of claim 8 further comprising:
    (iii) at least one barrier layer positioned over the layer, said barrier layer comprising a second polymer matrix having a thickness adequate to provide controlled release of the deuterated rapamycin.

10. The medical device of claim 9 wherein the at least one barrier layer includes a bioactive agent.

11. The medical device of claim 1, wherein the medical device is a device that is selected from the group consisting of a catheter, wire guide, cannula, stent graft, covered stent, vascular or other graft, cardiac pacemaker lead or lead tip, an angioplasty device, or portion thereof.

* * * * *